United States Patent
Reinstein et al.

(10) Patent No.: US 12,138,115 B1
(45) Date of Patent: Nov. 12, 2024

(54) SYSTEM OF DETERMINING THE CORRECT IMPLANTABLE COLLAMER LENS SIZE FROM ULTRASOUND IMAGES OF THE EYE

(71) Applicant: Dan Z Reinstein, San Ramon, CA (US)

(72) Inventors: Dan Z. Reinstein, London (GB); Ryan Vida, London (GB); Timothy James Archer, London (GB)

(73) Assignee: Dan Z. Reinstein, London (GB)

( * ) Notice: Subject to any disclaimer, the term of this patent is extended or adjusted under 35 U.S.C. 154(b) by 0 days.

(21) Appl. No.: 17/066,473

(22) Filed: Oct. 8, 2020

Related U.S. Application Data

(60) Provisional application No. 62/913,740, filed on Oct. 11, 2019.

(51) Int. Cl.
*A61B 8/10* (2006.01)
*A61B 8/08* (2006.01)
*A61F 2/16* (2006.01)

(52) U.S. Cl.
CPC .............. *A61B 8/10* (2013.01); *A61B 8/5215* (2013.01); *A61F 2/16* (2013.01)

(58) Field of Classification Search
CPC ............ A61B 8/10; A61B 8/5215; A61F 2/16
See application file for complete search history.

(56) References Cited

U.S. PATENT DOCUMENTS

| | | | |
|---|---|---|---|
| 2007/0260157 A1* | 11/2007 | Norrby | A61B 3/0025 600/558 |
| 2016/0074007 A1* | 3/2016 | Fedor | A61F 2/16 600/452 |
| 2016/0302660 A1 | 10/2016 | Bühren et al. | |

OTHER PUBLICATIONS

Dougherty PJ, Rivera RP, Schneider D, Lane SS, Brown D, Vukich J. Improving accuracy of phakic intraocular lens sizing using high-frequency ultrasound biomicroscopy. J Cataract Refract Surg. Jan. 2011;37(1):13-8. doi:10.1016/j.jcrs.2010.07.014. Epub Nov. 3, 2010. PMID: 21050711 (Year: 2011).*

Dougherty et al., "Improving accuracy of phakic intraocular lens sizing using high-frequency ultrasound biomicroscopy", J Cataract Refract Surg, vol. 37, Jan. 2011 (Year: 2011).*

(Continued)

*Primary Examiner* — Patrick Fernandes
*Assistant Examiner* — Aminah Asghar
(74) *Attorney, Agent, or Firm* — Fitch, Even, Tabin & Flannery LLP

(57) ABSTRACT

A method for operating a data processing system to provide an estimate of a vault value for a PIOL to be inserted in a patient, a system for predicting the vault that will be realized for an implant, and computer readable medium that includes instructions that cause a data processing system to implement the method when the instructions are executed by a data processing system are disclosed. The method includes causing the data processing system to receive ultrasound-based anatomical measurements of the patient's eye, causing the data processing system to receive parameters specifying a power and size for the PIOL; and utilizing a calibrated model of a human eye to predict the vault based on the anatomical measurements and the parameters specifying the power and the size for the PIOL.

10 Claims, 4 Drawing Sheets

(56) References Cited

OTHER PUBLICATIONS

Tehrani, et al., Preoperative Simulation of Postoperative Iris-Fixated Phakic Intraocular Lens Position and Simulation of Aging Using High-Resolution Scheimpflug Imaging, Journal of Cataract & Refractive Surgery, vol. 33, Jan. 2007.
Preliminary Report on Patentability, International Application No. PCT/US2021/029030, dated Nov. 10, 2022.
Pop et al; "Predicting Sulcus Size Using Ocular Measurements"; J Cataract Refract Surg; vol. 27, Jul. 2001; pp. 1033-1038.
Reinstein et al; "Correlation of Anterior Chamber Angle and Ciliary Sulcus Diameters with White-to-White Corneal Diameter in High Myopes Using Artemis VHF Digital Ultrasound"; Journal of Refractive Surgery; vol. 25, Feb. 2009; pp. 185-194.
Oh et al; "Direct Measurement of the Ciliary Sulcus Diameter by 35-Megahertz Ultrasound Biomicroscopy"; Ophthalmology, vol. 114, No. 9; Sep. 2007; pp. 1685-1688.
Kim et al; "Correlation Between Ciliary Sulcus Diameter Measured by 35 MHz Ultrasound Biomicroscopy and Other Ocular Measurements"; J Cataract Refract Surg 2008; vol. 34, Apr. 2008; pp. 632-637.
Kojima et al; "Optimization of an Implantable Collamer Lens Sizing Method Using High-Frequency Ultrasound Biomicroscopy"; American Journal of Ophthalmology; vol. 153, No. 4; Apr. 2012; pp. 632-637.
Baikoff et al; "Crystalline Lens Rise and Pigment Dispersion With Artisan Phakic Lenses"; J Cataract Refract Surg, vol. 31, Apr. 2005; pp. 674-680.
Igarashi et al; "Predictability of the Vault After Posterior Chamber Phakic Intraocular Lens Implantation Using Anterior Segment Optical Coherence Tomography"; J Cataract Refract Surg 2019; vol. 45, Issue 8, Aug. 2019; pp. 1099-1104.
Malyugin et al; "Posterior Chamber Phakic intraocular Lens Sizing Based on Iris Pigment Layer Measurements by Anterior Segment Optical Coherence Tomography"; J Cataract Refract Surg 2015; vol. 41, Aug. 2015; pp. 1616-1622.
Nakamura et al; "Implantable Collamer Lens Sizing Method Based on Swept-Source Anterior Segment Optical Coherence Tomography"; American Journal of Ophthalmology, vol. 187, Mar. 2018; pp. 99-107.
Reinstein et al; "Accuracy, Repeatability, and Reproducibility of Artemis Very High-Frequency Digital Ultrasound Arc-Scan Lateral Dimension Measurements"; J Cataract Refract Surg, vol. 32, Nov. 2006; pp. 1799-1802.
Reinstein et al; "Comparison of Postoperative Vault Height Predictability Using White-to-White or Sulcus Diameter-Based Sizing for the Visian Implantable Collamer Lens"; Journal of Refractive Surgery, vol. 29, No. 1, 2013; pp. 30-35.
Zhang et al; "Analysis of Intraocular Positions of Posterior Implantable Collamer Lens by Full-Scale Ultrasound Biomicroscopy"; BMC Ophthalmology; 2018; 11 pages.
Kato et al; "Vault Changes Caused by Light-Induced Pupil Constriction and Accomodation in Eyes With an Implantable Collamer Lens"; Cornea, vol. 38, No. 2, Feb. 2019; pp. 217-220.
Chen et al; "Comparison of Early Changes in and Factors Affecting Vault Following Posterior Chamber Phakic Implantable Collamer Lens Implantation Without and With a Central Hole (ICL V4 and ICL V4c)"; BMC Ophthalmology; 2016; 9 pages.
Werner et al; "Correlation Between Different Measurements Within the Eye Relative to Phakic Intraocular Lens Implantation"; J Cataract Refract Surg, vol. 30, Sep. 2004; pp. 1982-1988.
Reinstein et al; "New Sizing Parameters and Model for Predicting Postoperative Vault for the Implantable Collamer Lens Posterior Chamber Phakic Intraocular Lens"; Journal of Refractive Surgery, vol. 38, No. 5, 2022; pp. 272-286.

* cited by examiner

SYSTEM OF DETERMINING THE CORRECT IMPLANTABLE COLLAMER LENS SIZE FROM ULTRASOUND IMAGES OF THE EYE

RELATED APPLICATIONS

This application claims priority from U.S. Provisional Application No. 62/913,740 filed Oct. 11, 2019.

BACKGROUND

A phakic intraocular lens (PIOL), such as the implantable collamer lens, is an attractive alternative for some patients seeking decreased dependence on glasses and/or contact lenses. The PIOL is inserted surgically between the patient's crystalline lens and the iris. The separation between the anterior surface of the patient's crystalline lens and the back of the PIOL is known as lens separation or "vault". Selecting the correct size for the PIOL presents significant challenges. Problems may arise if the size of the PIOL implanted is too large (resulting in very high vault) or too small (resulting in very low or no vault).

If the size of the implanted PIOL is too large and the resulting vault is too high then the PIOL may push the iris forward. This can lead to narrowing of the anterior chamber angle which may increase the risk for intraocular pressure changes with subsequent irreversible glaucomatous nerve damage. In addition, the back surface of the iris, the pigment epithelium of the iris, can be excessively rubbed/chaffed against by the oversized PIOL causing the pigment of the iris to rub off and disperse into the anterior chamber. Unwanted pigment cells in the anterior chamber may affect the trabecular meshwork causing increased fluid outflow resistance, an increase in intraocular pressure and glaucomatous nerve damage.

If the size of the implanted PIOL is too small and the resulting vault is too low, then the PIOL may come into contact with the anterior surface of the crystalline lens. This may result in early cataract formation. In addition, if the vault of the PIOL is too low (even if not touching the anterior surface of the crystalline lens), then it may interfere with the flow of nutrients to the crystalline lens which also may contribute to early cataract formation.

Selecting the correct PIOL lens size is complicated by two factors. First, these lenses are only available in discrete size increments. Second, the anatomical structures on which the PIOL haptics and footplates ("feet") rest are not visible using optical methods (e.g. optical coherence tomography) because the iris is not transparent to light. Accordingly, the basic standard method for selecting the lens size is to use the horizontal white-to-white diameter, under the assumption that this is sufficiently correlated to the dimensions of the posterior chamber, the space behind the iris, to yield a reasonable and safe vault between the PIOL from the natural crystalline lens. However, multiple studies have shown that there is only a very weak correlation between white-to-white and the internal posterior chamber sulcus-to-sulcus distance. Therefore, various investigators have attempted to find optically visible measurements, such as the anterior chamber angle diameter, that can be used to improve the prediction to posterior chamber dimensions and improve upon lens size recommendations. These attempts have only been partially successful in predicting the vault values.

SUMMARY

Figure 1:
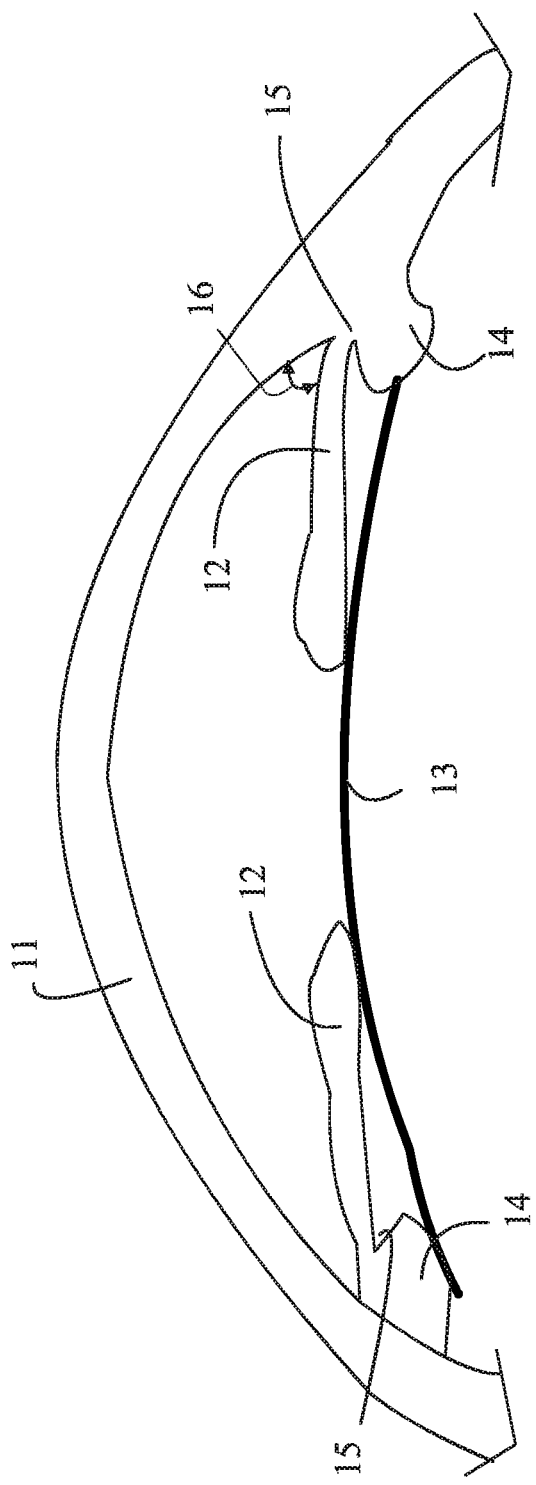
FIG. 1 is a cross-sectional view of a portion of an eye illustrating the structures that are relevant to a PIOL implant.

The present invention includes a method for operating a data processing system to provide an estimate of a vault value for a PIOL to be inserted in a patient, a system for predicting the vault that will be realized for an implant, and computer readable medium that includes instructions that cause a data processing system to implement the method when the instructions are executed by a data processing system. The method includes:

causing the data processing system to receive ultrasound-based anatomical measurements of the patient's eye, causing the data processing system to receive parameters specifying a power and size for the PIOL; and utilizing a calibrated model of a human eye to predict the vault based on the anatomical measurements and the parameters specifying the power and the size for the PIOL and displaying said vault to a user of said data processing system to determine if said vault is satisfactory for said patient.

In one aspect, the data processing system receives the ultrasound-based anatomical measurements which include causing the data processing system to receive an ultrasound image of the patient's eye and determining the ultrasound-based anatomical measurements from the ultrasound image.

In one aspect, the anatomical measurements comprise measurements of the diameter of the plane passing through the ciliary body (CBID).

In one aspect, the anatomical measurements comprise measurements of the sulcus-to-sulcus-lens-rise (STSL).

In one aspect, the anatomical measurements comprise measurements of the scotopic pupil diameter (SPD).

In one aspect, the calibrated model is a linear model.

A system according to the present invention includes a data processing system and an ultrasound imaging device. The ultrasound imager is adapted for providing an image of a patient's eye, and the data processing system receiving a plurality of anatomical measurements of a patient's eye from the image, receiving parameters specifying a power and size for a PIOL; and providing a measurement of a vault for the patient's eye utilizing a calibrated model of a human eye to predict the vault based on the anatomical measurements and the parameters specifying a power and the a size for the PIOL.

In one aspect, the anatomical measurements comprise measurements of CBID.

In one aspect, the anatomical measurements comprise measurements of STSL.

In one aspect, the anatomical measurements comprise measurements of SPD.

The computer readable medium stores instructions that cause a data processing system to execute a method for operating a data processing system to provide an estimate of a vault value for an ICL to be inserted in a patient. The method includes causing the data processing system to receive ultrasound-based anatomical measurements of the patient's eye; causing the data processing system to receive parameters specifying a power and size for the ICL; and utilizing a calibrated model of a human eye to predict the vault based on the anatomical measurements and the parameters specifying the power and the size for the ICL.

In one aspect, causing the data processing system to receive the ultrasound-based anatomical measurements includes causing the data processing system to receive an ultrasound image of the patient's eye and determining the ultrasound-based anatomical measurements from the ultrasound image.

In one aspect, the anatomical measurements comprise measurements of CBID.

In one aspect, the anatomical measurements comprise measurements of STSL.

In one aspect, the anatomical measurements comprise measurements of SPD.

In one aspect, the calibrated model is a linear model.

DETAILED DESCRIPTION

The manner in which the present invention provides its advantages can be more easily understood with reference to FIG. 1 which is a cross-sectional view of a portion of an eye illustrating the structures that are relevant to a PIOL implant. The cornea is shown at 11. The upper surface of the capsule containing the crystalline lens is shown at 13. The iris 12 rests on the upper surface of the capsule. The angle between the iris and the inner surface of the cornea is shown at 16. The ciliary body is shown at 14. The sulcus is shown at 15.

Figure 2:
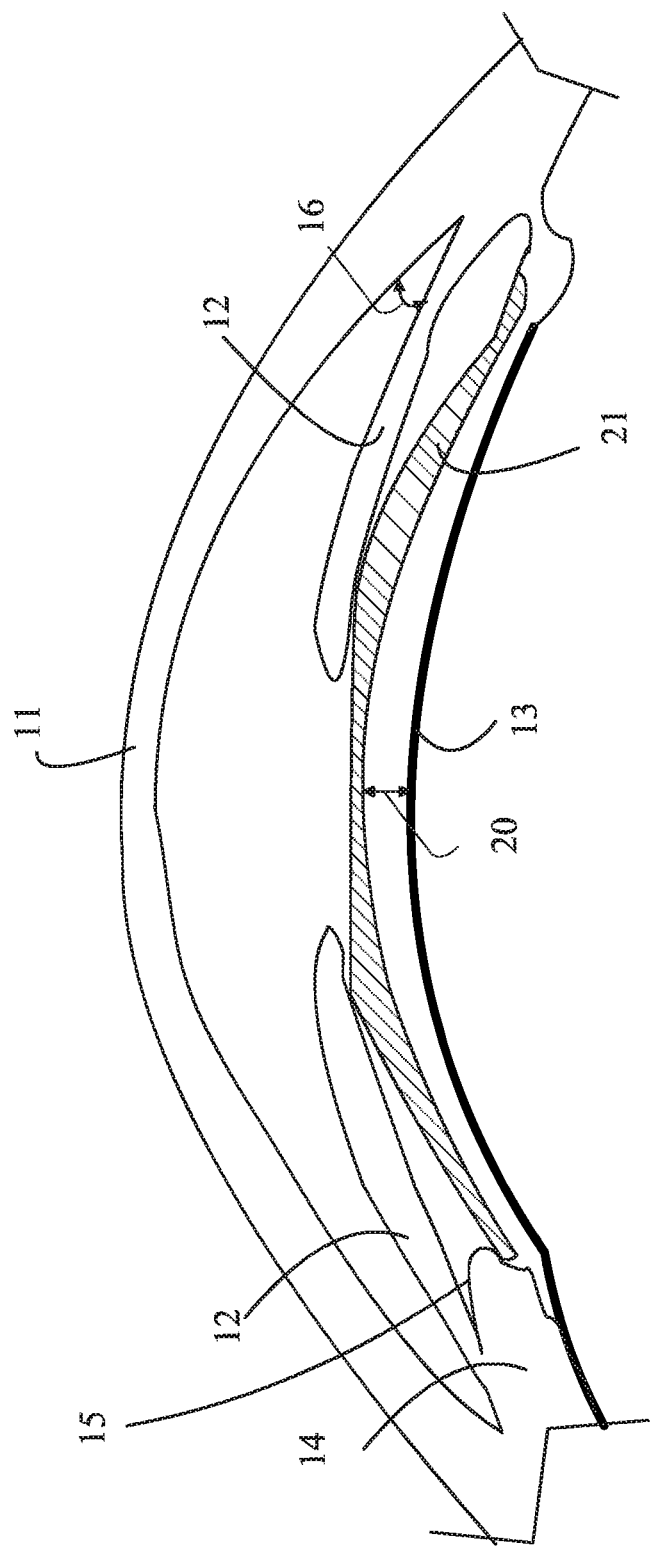
FIG. 2 illustrates the region of the eye shown in FIG. 1 after the insertion of a PIOL.

Refer now to FIG. 2, which illustrates the region of the eye shown in FIG. 1 after the insertion of a PIOL 21. The PIOL is inserted between the crystalline lens and the iris 12. The feet of the PIOL rest on the ciliary body. PIOL 21 vaults over crystalline lens capsule 13 as shown at 20. As a result, the portion of the iris nearest the pupil is moved towards the cornea. This results in the angle 16 decreasing. The greater the vault 20, the smaller the angle 16 becomes. In addition, the posterior surface of the iris 12 in contact with the PIOL 21 can rub in a manner which results in pigment being released from the iris. The higher the vault, the greater the abrasive forces that can lead to such a release.

If, on the other hand, the vault is too low, the PIOL can rub on the anterior surface of the crystalline lens capsule 13, which can lead to early cataract formation. In addition, if the vault is too low, the PIOL 21 can interfere with the nutrient flow across the surface of the capsule which may also contribute to early cataract formation.

The feet of the PIOL rest on the ciliary body between the capsule and the sulcus. Increasing the size of the PIOL increases the vault, since the PIOL must bend upward to accommodate the greater length.

The problem of predicting the vault for a given PIOL size is complicated by the fact that the eye parameters that can be directly measured by optical methods do not include direct measurements of structures behind the iris, since the iris blocks visible light. While there are correlations between the visibly measurable parameters and the structures behind the iris, the correlations are not sufficiently strong to provide the desired accuracy in some eyes.

One method for improving the prediction of the vault for a given PIOL size utilizes high-frequency ultrasound to image the eye. Since sound waves are not blocked by the optically opaque portions of the iris, direct measurements of the structures in the posterior chamber of the eye can be made.

Figure 3:
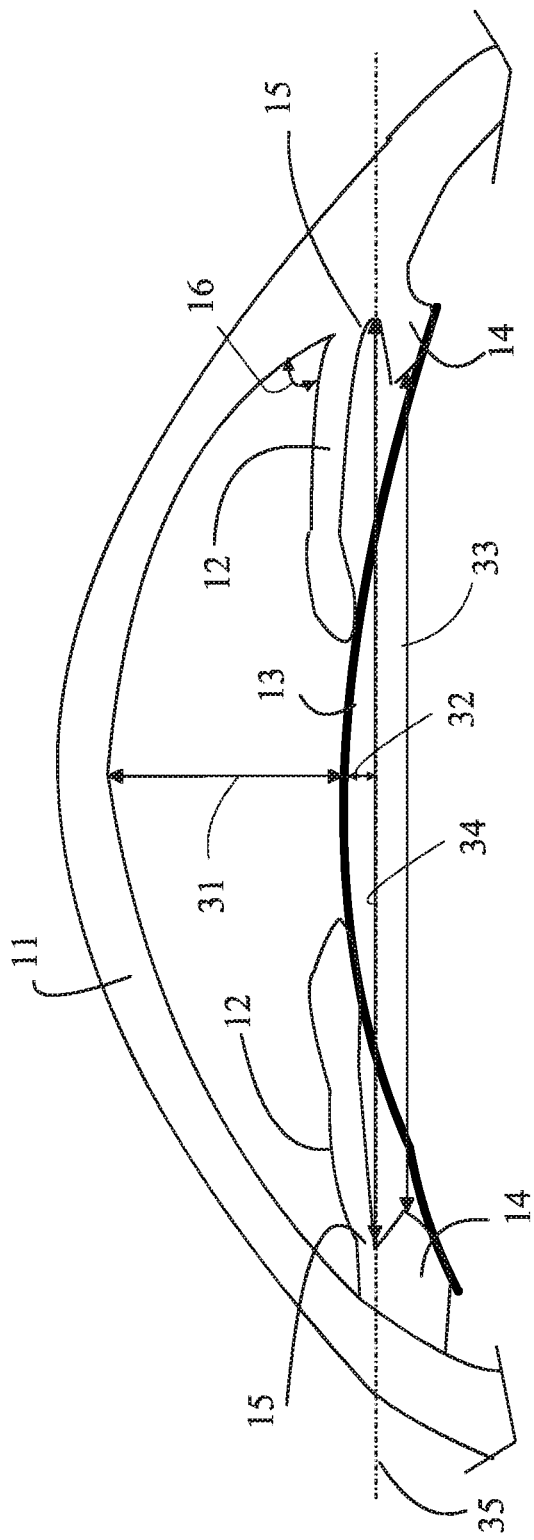
FIG. 3 is cross-sectional view of the anterior portion of a human eye.

While methods for predicting the vault from measurements made with ultrasound imaging have been suggested, the accuracy with which the vault height is predicted is still insufficient for some purposes. The manner in which the methods that use ultrasound images for part of the parameters used to compute the vault for various lens sizes can be more easily understood with reference to FIG. 3, which is cross-sectional view of the anterior portion of a human eye. It should be noted that the eye is spherical, and hence, many of the structures are circular in conformation.

One easily identifiable "landmark" is the sulcus. The plane 35 passing through the sulcus is used to define three measurements of interest. The sulcus-to-sulcus distance (STS) is shown at 34. This is essentially the diameter of the ring of the sulcus. The maximum distance 32 from the plane defined by the sulcus to the anterior edge of the capsule will be referred to as the STSL. The distance 31 from the capsule to the anterior portion of the cornea will be referred to as the anterior chamber depth (ACD). The diameter 33 of the plane passing through the CBID is also predictive.

In addition to the parameters that depend on behind the iris imaging, it has been found that the SPD has predicative value in determining the vault or finding a lens size that provides the desired vault. The SPD is the diameter of the pupil under scotopic light conditions, and is related to PIOL vault due to the difference in force exerted by the iris onto the PIOL for small and large pupils. The pupil size varies according to lighting conditions such that in bright light the pupil constricts and in dim light it dilates. Therefore, depending on lighting conditions and according to how lighting changes during the day the pupil size will be different and produce a specific change in the separation between the PIOL and the crystalline lens. Scotopic pupil size is defined as the pupil diameter under scotopic lighting conditions, defined as ambient 0.04 lux. In addition, the lens size and PIOL power need to be taken into account. The lens size is the diagonal diameter of the lens to the tip of the haptics. A recommended PIOL lens size is provided by the lens manufacturer. The PIOL power is related to the curvature of the inner surface of the PIOL. For example, a high powered myopic lens will have an increased radius of curvature of the back surface of the lens resulting in a higher central vault compared to a lower powered lens. PIOL. The PIOL power is also related to the thickness profile of the PIOL, and therefore, PIOLs with different powers react differently when forces are applied. Therefore PIOLs having different powers (assuming all other conditions are identical) will result in different vault outcomes.

The parameters CBID, SPD, STS and STSL will be referred to as the anatomical parameters in the following discussion. The parameters PIOL power and PIOL size will be referred to as the target PIOL parameters.

In one aspect of the invention, a model that depends on the anatomical parameters, the target PIOL parameters and a set of unknown parameters is trained by fitting a data set derived by measuring the number of different patients before and after PIOL implants. In the training mode, the a prior art system for predicting the vault is utilized to minimize the risk of an improperly sized PIOL being implanted into a patient. Once a data set with sufficient statistical accuracy to provide improved accuracy is accumulated, the improvement available with the present system can be realized.

One exemplary model relates the vault of the PIOL to a linear function of the above parameters, e.g.

$$\text{Predicated Vault} = a + \text{CBID} + b*\text{STSL} + c*(\text{PIOL Power}) + d*(\text{PIOL size}) + e*\text{SPD}$$

The parameters a-e are determined by fitting the observed vault values in the patient group.

While the above-described embodiments utilize a linear model for the relationship between the vault, the measured parameters and desired lens parameters, other functional relationships could be utilized. In addition, the measured parameters could be replaced by other measured quantities that are tightly correlated with the above-described measured parameters.

In some embodiments, the user wishes to find the closest lens size of the desired power from among a finite set of lens sizes. PIOLs are typically manufactured in discrete lens sizes, which differ from one another in steps of approximately 0.5 mm. In one exemplary embodiment, the system of the present disclosure provides a vault value for each PIOL size in some predetermined set of PIOLs.

In other embodiments, the users may wish to know the ideal PIOL size to obtain the desired vault. If sufficient intermediate sizes are found to be of benefit, the results of the current model could be used to alter the choices provided by the manufacturer of the PIOLs.

Once the model is calibrated, the system of the present invention can be practiced on a general purpose computer that is adapted to receive high frequency ultrasound images or on the controller that is included in most high frequency ultrasound devices. In addition, a general purpose computer running the algorithm of the present system can be configured to receive the anatomical measurements and desired PIOL power from a user without the need to extract the anatomical measurements from the ultrasound images. In this case, the anatomical measurements can be provided by the imaging system or by an operator of that system.

Many small eye clinics do not have high frequency ultrasound devices, since many of the measurements normally performed in those clinics utilize optical scanning. Accordingly, a clinic that wishes to utilize the system of the present disclosure may send the patient to a central testing facility that will perform the ultrasound imaging of the patient's eyes and return the scans to the clinic for processing on the clinic's computers. In some embodiments, the imaging center may include the model of the present invention as part of the returned images in the form of a computer readable medium. Alternatively, the controller on the ultrasound imaging device can provide the anatomical measurements required by the model and return that data to the clinic for processing together with the other measurements of the patient's eyes.

Figure 4:
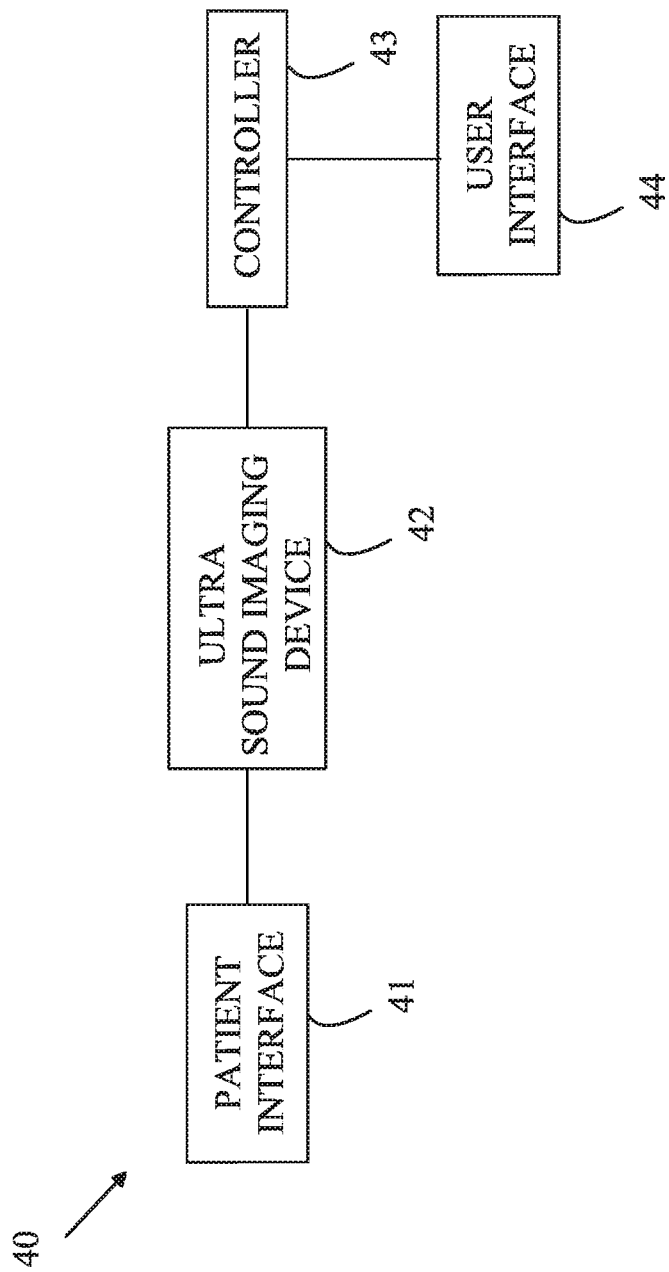
FIG. 4 illustrates one embodiment of an imaging system according to the present disclosure.

Refer now to FIG. 4, which illustrates one embodiment of an imaging system according to the present disclosure. In system 40, the imaging device forms the images of the patient's eyes using ultrasound imaging device 42 that is coupled to the patient's eye by patient interface 41. The recorded image is processed by controller 43, which extracts the anatomical measurements that depend on the ultrasound image. A user interface 44 allows a user to input additional information such as the PIOL power and possible sizes to controller 43. Controller 43 computes the predicted vault for each lens size requested by the user.

As noted above, the data processing functions of controller 43 can be implemented on a separate data processing system which is adapted to receive ultrasound images from a separate ultrasound imaging device. A user interface of that separate data processing system can be used for inputting the lens properties and outputting the predicted vaults for each desired lens size.

The present invention also includes a computer readable medium that stores instructions that cause a data processing system to execute the method of the present invention. A computer readable medium is defined to be any medium that constitutes patentable subject matter under 35 U.S.C. 101 and excludes any medium that does not constitute patentable subject matter under 35 U.S.C. 101. Examples of such media include non-transitory media such as computer memory devices that store information in a format that is readable by a computer or data processing system.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. A method for operating a data processing system to provide a vault value for a PIOL, characterized by a front surface and a back surface, to be inserted in a patient's eye between a crystalline lens, characterized by an anterior surface and a posterior surface and an iris, said method comprising:
   causing said data processing system to receive a plurality of high-frequency ultrasound-based anatomical measurements of said patient's eye, wherein said plurality of anatomical measurements includes CBID;
   causing said data processing system to receive a parameter specifying a power for said PIOL;
   causing said data processing system to receive a parameter specifying a size for said PIOL;
   [a] computing predicted vault value by using a function of said plurality of anatomical measurements and said parameters specifying said power and said size for said PIOL, wherein said function comprises a*CBID+b*STSL+c*(PIOL Power)+d*(PIOL size)+e*SPD, wherein parameters a, b, c, d, and e are determined by fitting observed vault values in a patient group, said vault value being a separation between said anterior surface of said patient's crystalline lens and said back surface of said PIOL;
   [b] implanting said PIOL in said patient's eye if said predicted vault value is within a desired range; and if said predicted vault value is not within said desired range, causing
   said data processing system to receive a parameter specifying a different size for said PIOL; and
   upon receiving the parameter specifying the different size for said PIOL repeating steps [a]-[b] with said different size.

2. The method of claim 1 wherein causing said data processing system to receive said plurality of high-frequency ultrasound-based anatomical measurements comprises causing said data processing system to receive a high-frequency ultrasound image of said patient's eye and determining said plurality of high-frequency ultrasound-based anatomical measurements from said high-frequency ultrasound image.

3. The method of claim 1 wherein said plurality of anatomical measurements comprises measurements of STSL and SPD.

4. The method of claim 1 wherein said function is a linear function.

5. A system for predicting a PIOL vault value, comprising a data processing system and a high-frequency ultrasound imaging device,
   said high-frequency ultrasound imaging device being connected to said data processing system and being adapted for providing an image of a patient's eye to said data processing system, and said data processing system being configured for:

extracting a plurality of anatomical measurements of said patient's eye from said image wherein said plurality of anatomical measurements includes CBID, said image of said patient's eye including a crystalline lens characterized by an anterior surface and a posterior surface, said data processing system also receiving parameters specifying a power and a size for a PIOL to be implanted in said patient's eye, said PIOL being characterized by a front surface and a back surface;

computing a predicted vault value for said patient's eye by using a function of said anatomical measurements and said parameters specifying said power and said size for said PIOL, wherein said function comprises a*CBID+b*STSL+c*(PIOL Power)+d*(PIOL size)+e*SPD, wherein parameters a, b, c, d, and e are determined by fitting observed vault values in a patient group, said vault value being a separation between said anterior surface of said patient's crystalline lens and said back surface of said PIOL;

displaying the predicted vault value to a user of said data processing system, whereby the user implants said PIOL in said patient's eye if said predicted vault value is within a desired range.

6. The system of claim 5 wherein said plurality of anatomical measurements comprises measurements of SPD and STSL.

7. A computer readable medium containing instructions that cause a data processing system to execute a method for operating a data processing system to predict a vault value for a PIOL characterized by a front surface and a back surface, said PIOL to be inserted in a patient's eye between a crystalline lens and an iris, said crystalline lens characterized by an anterior surface and a posterior surface, said method comprising:

causing said data processing system to receive a plurality of high-frequency ultrasound-based anatomical measurements of said patient's eye, wherein said plurality of anatomical measurements includes CBID;

causing said data processing system to receive a parameter specifying a power for said PIOL;

causing said data processing system to receive a parameter specifying a size for said PIOL;

[a] computing a predicted vault value by using a function of said plurality of anatomical measurements and said parameters specifying said power and said size for said PIOL, wherein said function is a*CBID+b*STSL+c*(PIOL Power)+d*(PIOL size)+e*SPD, wherein parameters a, b, c, d, and e are determined by fitting observed vault values in a patient group, said vault value being a separation between said anterior surface of said patient's crystalline lens and said back surface of said PIOL;

[b] implanting said PIOL in said patient's eye if said predicted vault value is within a desired range; and if said predicted vault value is not within said desired range, causing said data processing system to receive a parameter specifying a different size for said PIOL; and upon receiving the parameter specifying the different size for said PIOL, repeating steps [a]-[b] with said different size.

8. The computer readable medium of claim 7 wherein causing said data processing system to receive said high-frequency ultrasound-based plurality of anatomical measurements comprises causing said data processing system to receive a high-frequency ultrasound image of said patient's eye and determining said high-frequency ultrasound-based plurality of anatomical measurements from said high-frequency ultrasound image.

9. The computer readable medium of claim 7 wherein said high-frequency ultrasound-based plurality of anatomical measurements comprises measurements of STSL and SPD.

10. The computer readable medium of claim 7 wherein said function is linear with respect to each of CBID, STSL, and SPD.

* * * * *